United States Patent
Laufer et al.

(10) Patent No.: US 9,428,611 B2
(45) Date of Patent: Aug. 30, 2016

(54) CATALYSTS FOR PRODUCING CAST POLYAMIDE, METHOD FOR THE PRODUCTION OF SAID CATALYSTS AND THE USE THEREOF

(71) Applicant: Rhein Chemie Rheinau GmbH, Mannheim (DE)

(72) Inventors: Wilhelm Laufer, Ellerstadt (DE); Serdar Uestuenbas, Mannheim (DE)

(73) Assignee: Rhein Chemie Rheinau GmbH, Mannheim (DE)

( * ) Notice: Subject to any disclaimer, the term of this patent is extended or adjusted under 35 U.S.C. 154(b) by 0 days.

(21) Appl. No.: 14/411,632

(22) PCT Filed: Jun. 6, 2013

(86) PCT No.: PCT/EP2013/061726
§ 371 (c)(1),
(2) Date: Dec. 29, 2014

(87) PCT Pub. No.: WO2014/005791
PCT Pub. Date: Jan. 9, 2014

(65) Prior Publication Data
US 2015/0322204 A1    Nov. 12, 2015

(30) Foreign Application Priority Data
Jul. 6, 2012   (EP) .................... 12175416

(51) Int. Cl.
C08G 69/20    (2006.01)
C07C 63/28    (2006.01)
C08G 75/02    (2016.01)

(52) U.S. Cl.
CPC .............. *C08G 69/20* (2013.01); *C07C 63/28* (2013.01); *C08G 75/025* (2013.01)

(58) Field of Classification Search
CPC ............................ C07C 63/28; C08G 75/025
See application file for complete search history.

(56) References Cited

U.S. PATENT DOCUMENTS

| 2,840,589 | A | | 6/1958 | Smeltz | |
| 3,037,003 | A | * | 5/1962 | Griehl | C08G 69/20 528/312 |
| 3,663,670 | A | * | 5/1972 | Swayne | C08J 9/12 264/236 |
| 4,031,164 | A | * | 6/1977 | Hedrick | C08G 69/44 525/420 |
| 1,160,080 | A | | 7/1979 | Koenig et al. | |
| 4,595,747 | A | * | 6/1986 | Gabbert | C08G 69/20 525/420 |
| 7,067,654 | B2 | | 6/2006 | Richter et al. | |
| 8,802,809 | B2 | | 8/2014 | Laufer et al. | |
| 2012/0071648 | A1 | * | 3/2012 | Laufer | C08G 69/20 540/533 |

FOREIGN PATENT DOCUMENTS

DE    1130594 B    5/1962

OTHER PUBLICATIONS

International Search Report from International Application No. PCT/EP2013/061726, dated Jul. 15, 2013, two pages.

* cited by examiner

*Primary Examiner* — Gregory Listvoyb

(57) ABSTRACT

The present invention relates to novel catalysts for the production of cast polyamide, to processes for production thereof and to the use thereof.

15 Claims, No Drawings

CATALYSTS FOR PRODUCING CAST POLYAMIDE, METHOD FOR THE PRODUCTION OF SAID CATALYSTS AND THE USE THEREOF

The present invention relates to novel catalysts for the production of cast polyamide, to processes for production thereof and to the use thereof.

Cast polyamides are polyamides of particularly high molecular weight. In the production of cast polyamides, a lactam is poured into a mold together with at least one catalyst and at least one activator and then anionically polymerized in this mold. This involves polymerization of the starting compounds present in the mold, generally with heating. This gives rise to a homogeneous material which is superior to extruded polyamides in terms of crystallinity.

Cast polyamides are suitable as thermoplastics for the production of complex components. In contrast to many other thermoplastics, there is no need to melt them; instead, they form through anionic polymerization of the lactam in a mold at 120 to 150° C. within just a few minutes. This can be done by any known casting method, such as stationary casting, injection casting, rotary casting and centrifugal casting. The end products obtained in each case are moldings of a crystalline polyamide of high molecular weight which features a low weight, high mechanical durability, very good sliding properties and excellent chemical resistance, and which—since the molds are not filled under pressure—has only low internal stresses. Cast polyamides can be sawed, drilled, machined, ground, welded and printed or painted; as well as complex hollow molds, examples of other articles produced from this polymer are rollers for passenger elevators and semifinished products, for example tubes, bars and sheets for mechanical engineering and the automobile industry.

The production of cast polyamide parts proceeding from low-viscosity lactam melts and a catalyst, and also an activator, by what is called activated anionic polymerization is known per se. For this purpose, it is customary to commix two mixtures of catalyst and lactam and of activator and lactam in the form of a liquid melt and then to polymerize them in the casting mold; see EP-A-2447302. However, a disadvantage of the current catalysts for cast polyamides is the excessively high and non-constant reactivity. This leads to comparatively poor product properties, for example low crystallinity, and makes the procedure uneconomic, particularly for large castings.

It was thus an object of the present invention to provide novel compositions which are suitable as catalysts in the production of cast polyamides, and which do not have the disadvantages of the prior art.

It has now been found that, surprisingly, the inventive compositions have this profile of properties.

The present invention thus provides compositions comprising
 a) at least one lactamate and
 b) at least one salt and/or ester of an organic acid substituted by heteroatoms, and optionally
 c) at least one lactam.

In a preferred embodiment of the invention, lactamates a) are at least one compound selected from the group of the alkali metal aluminodilactamates and alkali metal and/or alkaline earth metal lactamates.

Preferred lactamates in the context of the invention are alkali metal and/or alkaline earth metal lactamates, preferably sodium, potassium and/or magnesium, individually or in a mixture.

The aforementioned lactamates are commodity chemicals and are available, for example from Rhein Chemie Rheinau GmbH.

In a preferred embodiment of the invention, the ester b) comprises $C_1$-$C_6$-alkyl esters, preferably methyl and/or ethyl esters. The organic acid substituted by heteroatoms has preferably 1-12 carbon atoms, more preferably 4-6 carbon atoms.

In a preferred embodiment of the invention, the salt of an organic acid b) substituted by heteroatoms, preferably amino groups, has 1-12 carbon atoms, more preferably 4-6 carbon atoms.

In a particularly preferred embodiment of the invention, the heteroatoms are nitrogen, sulfur, phosphorus, preferably nitrogen, more preferably amino groups, and/or halides, preferably chlorine and/or bromine.

More preferably, the salt and/or ester of an organic acid b) substituted by heteroatoms comprises aminocapronates and/or aminolaurates, preferably alkali metal and/or alkaline earth metal aminocapronates and/or -laurates, more preferably sodium aminocapronate, potassium aminocapronate and/or magnesium aminocapronate.

In a preferred embodiment of the invention, the lactam c) is a compound of the general formula

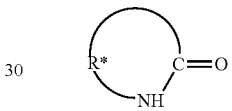

where R* is an alkylene group having 3 to 13 carbon atoms.

Preference is given here to caprolactam and/or laurolactam. These are commercially available, for example from Lanxess Deutschland GmbH.

The inventive composition preferably includes constituents a) and b) in a ratio of 3:1 to 50:1, preferably 5:1 to 40:1, more preferably 9:1.

The proportion of lactam c), based on constituents a) and b), is preferably 0-99% by weight, more preferably 50-85% by weight.

The invention further provides a process for preparing the inventive composition, in which the lactamate a) is prepared by reaction of at least one lactam which corresponds to or else may be different than lactam c) with alkali metal or alkaline earth metal alkoxides in the presence of at least one salt and/or ester of an organic acid b) substituted by heteroatoms with subsequent or simultaneous removal of the alcohol formed by distillation, and then further lactam c) is optionally added.

In a preferred embodiment of the process according to the invention, the lactamate a) is prepared by reaction of lactam, preferably caprolactam, which corresponds to or else may be different than lactam c), with sodium methoxide in the presence of sodium aminocapronate and/or sodium aminolaurate b) with subsequent or simultaneous removal of the alcohol formed by distillation, and then further lactam c) is optionally added.

In a further preferred embodiment of the process according to the invention, the lactamate a) is prepared by reaction of at least one caprolactam in excess, which corresponds to lactam c), with sodium methoxide in the presence of sodium aminocapronate and/or sodium aminolaurate b) with subsequent or simultaneous removal of the alcohol formed by distillation.

The aforementioned reactions, i.e. the preparation of the lactamate and the distillation, are preferably performed at temperatures of 80-130° C.

The process according to the invention can be effected either as a batchwise process or in a continuous process. The salts and/or esters or organic acids may be added before, during and/or else after the preparation of the lactamate a).

Preference is likewise given to the process variant in which the salts and/or esters of the organic acids substituted by heteroatoms form "in situ". In a preferred embodiment of the invention, the salts and/or esters of the organic acids b) substituted by heteroatoms are prepared in situ by addition of acids, water and/or alkali metal and/or alkaline earth metal hydroxides to a) and optionally c). Particular preference is given to the addition of amounts of water required in stoichiometric terms to establish the desired salt concentrations.

In a further embodiment of the invention, the lactamate a) is melted at temperatures of 80-120° C. optionally together with lactam c), and admixed with at least one salt and/or ester of the organic acid b) substituted by heteroatoms, preferably while stirring.

For the stirring operation, it is possible to use standard stirrer units, such as preferably stirred tanks or mixers.

The invention further provides compositions obtainable by the aforementioned processes according to the invention. In relation to this subject-matter of the invention, reference is made to the above remarks, including all the preferred embodiments.

The invention likewise provides cast polyamides obtainable by the polymerization of lactams with at least one inventive composition composed of a) and b) and optionally c) at temperatures of 80-180° C., preferably of 120 and 160° C., in the presence of activators and optionally further additives and assistants.

The production is preferably effected by the shaping processes familiar to those skilled in the art, such as preferably injection casting, stationary casting and/or rotary casting.

The polymerization of lactams is preferably effected by addition of the inventive composition to the lactam which has been melted at temperatures of 80-120° C. and subsequent addition of a lactam melt comprising at least one activator and further additives and assistants.

This polymerization for production of the cast polyamides is preferably effected directly within the casting mold.

The polymerization is preferably effected with exclusion of air humidity, for example under reduced pressure or in an inert atmosphere.

Activators used in the context of the invention may be isocyanates, isocyanurates, biurets, allophanates, uretdiones and/or carbodiimides, as a single compound or in the form of a mixture. Likewise usable in the context of the invention are activators which have been blocked, for example by lactams, more preferably caprolactam, or by phenols, oximes and/or epoxides, and likewise solvent-containing activators. Suitable solvents are: N-alkylpyrrolidones, preferably N-methylpyrrolidone and N-ethylpyrrolidone, polyglycols, preferably polyglycol DME 200, dipropylene glycol DME or tetraethylene glycol DME.

Isocyanates in the context of the invention are preferably diisocyanates, more preferably 2,4-tolylene diisocyanate (TDI), 2,6-tolylene diisocyanate, a mixture of 2,4-tolylene diisocyanate and 2,6-tolylene diisocyanate, hexamethylene 1,6-diisocyanate, cyclohexane 1,4-diisocyanate, xylylene diisocyanate, isophorone diisocyanate, 1,5-naphthalene diisocyanate, 4,4'-diphenylmethane diisocyanate, 2,4'-diphenylmethane diisocyanate, 2,2'-diphenylmethane diisocyanate, 4,4'-diphenyldimethylmethane diisocyanate, 1,3-phenylene diisocyanate, 1,4-phenylene diisocyanate, dicyclohexylmethane 4,4'-diisocyanate, dicyclohexylmethane 2,4'-diisocyanate, dicyclohexylmethane 2,2'-diisocyanate, methylcyclohexane diisocyanate, tetramethylxylylene diisocyanate, 2,6-diisopropylphenylene isocyanate and mixtures thereof. Particular preference is given to hexamethylene 1,6-diisocyanate. The aforementioned compounds are commodity chemicals and are available, for example from Bayer MaterialScience AG.

Isocyanurates in the context of the invention are preferably compounds of the formula (I)

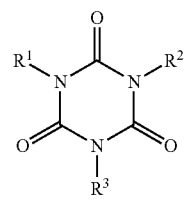

(I)

where $R^1$, $R^2$ and $R^3$ are each independently —$(CH_2)_m$—N=C=O or —$(CH_2)_q$—[$(C_6H_3)(Me/Et)_3(N=C=O)$], and m=1-12, q=0-6 and Me is methyl and Et is ethyl, where $R^1$, $R^2$ and $R^3$ are preferably the same.

Preference is given to the following compounds of the formula (II)

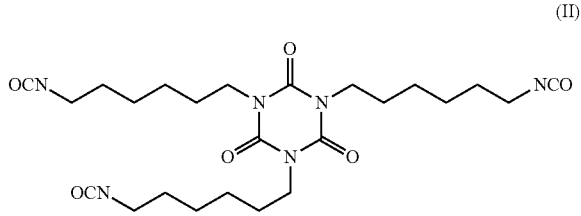

(II)

and of the formula (III)

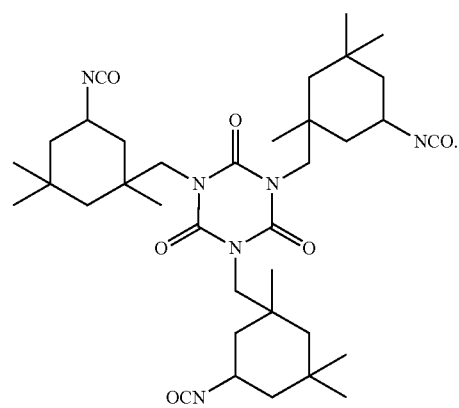

(III)

The aforementioned compounds are commodity chemicals and are available, for example from Bayer MaterialScience AG.

Biurets in the context of the invention are preferably compounds of the formula (IV)

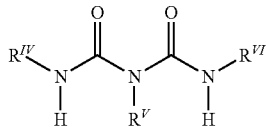

where $R^{IV}$, $R^{V}$ and $R^{VI}$ are each independently —$(CH_2)_p$—N=C=O, with p=1-12, where
$R^{IV}$, $R^{V}$ and $R^{VI}$ are preferably the same.

In a particularly preferred embodiment of the invention, the biuret is a compound of the formula (V), i.e. a biuret of the formula (IV) where $R^{IV}$, $R^{V}$ and $R^{VI}$=—$(CH_2)_p$—N=C=O and p=6

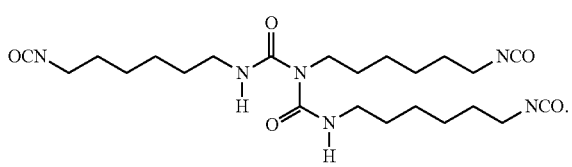

The aforementioned compounds are commodity chemicals and are available, for example from Bayer MaterialScience AG.

Uretdiones in the context of the invention are reaction products of at least two isocyanates with the formation of dioxodiazetidine bonds:

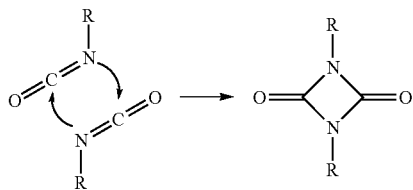

The preparation is known per se to those skilled in the art. The compounds can be prepared, for example, by the processes described in EP 1 422 223 A1.

The uretdione may be a dimer, trimer, oligomer or polymer.

Suitable examples of uretdiones are known per se to those skilled in the art. Preference is given to uretdiones which are obtained proceeding from an aliphatic or aromatic isocyanate. The aromatic isocyanates have, as R, preferably 6 to 20 carbon atoms, more preferably 6 to 15 carbon atoms. Corresponding aromatic monomeric isocyanates may be selected, for example, from the group consisting of 2,4-diisocyanatotoluene, 2,6-diisocyanatotoluene, 1,5-naphthylene diisocyanate, 4,4'-methylenediphenyl diisocyanate, 1,3-bis(3-isocyanato-4-methylphenyl)-2,4-dioxodiazetidine, N,N'-bis(4-methyl-3-isocyanatophenyl)urea and tetramethylxylylene diisocyanate. Of these aromatic isocyanates, preference is given to 2,4-diisocyanatotoluene, 2,6-diisocyanatotoluene and 4,4'-methylenebis(phenyl diisocyanate). Especially preferred are 2,6-diisocyanatotoluene and 4,4'-methylenebis(phenyl diisocyanate).

The aliphatic isocyanates have, as R, preferably 6 to 20 carbon atoms, more preferably 6 to 15 carbon atoms. Corresponding aliphatic monomeric isocyanates may be selected, for example, from the group consisting of isophorone diisocyanate, cyclohexyl 1,4-diisocyanate, 1,1-methylenebis(4-isocyanatocyclohexane), 1,2-bis(4-isocyanatononyl)-3-heptyl-4-pentyl-cyclohexane and hexamethylene 1,6-diisocyanate. Preference is given here to the use of isophorone diisocyanate and hexamethylene 1,6-diisocyanate.

The aforementioned compounds are commodity chemicals and are available, for example from Rhein Chemie Rheinau GmbH or Bayer MaterialScience AG.

Allophanates in the context of the invention are preferably compounds of the formula (VI)

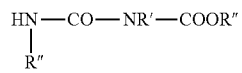

where R' and R'' are each independently an alkyl radical having 1 to 20 carbon atoms or an aryl radical having 6 to 20 carbon atoms,
and R''' is defined as an alkyl radical having 1 to 20 carbon atoms.

These compounds are generally obtainable by reaction of any desired starting compounds containing urethane and/or urea groups, containing units of the general formula (R''OOC—NHR'), with monoisocyanates of the general formula R'''—NCO or with diisocyanates of the general formula OCN-A-NCO, where R''' or A is preferably an alkyl radical having 1 to 20 carbon atoms or an aryl radical having 6 to 20 carbon atoms, and R' and R'' are each independently alkyl radicals having 1 to 20 carbon atoms or aryl radicals having 6 to 20 carbon atoms.

Suitable monoisocyanates are any desired aromatic, aliphatic and cycloaliphatic monoisocyanates having up to 20 carbon atoms, such as methyl isocyanate, isopropyl isocyanate, n-butyl isocyanate, n-hexyl isocyanate, cyclohexyl isocyanate, stearyl isocyanate, the optionally halogenated phenyl isocyanates, 1-naphthyl isocyanate, the optionally chlorinated or fluorinated m-, o- and p-tolyl isocyanates, p-isopropylphenyl isocyanate, 2,6-diisopropylphenyl isocyanate and p-toluenesulfonyl diisocyanate.

Suitable diisocyanates are any desired aromatic, aliphatic and cycloaliphatic diisocyanates having 6 to 40 carbon atoms, preferably 6 to 15 carbon atoms, such as more preferably isophorone diisocyanate, cyclohexyl 1,4-diisocyanate, 1,1-methylenebis(isocyanatohexane), 1,2-bis(4-isocyanatononyl)-3-heptyl-4-pentylcyclohexane, hexamethylene 1,6-diisocyanate, 2,4-diisocyanatotoluene, 2,6-diisocyanatotoluene, 1,5-naphthylene diisocyanate, 4,4'-methylenediphenyl diisocyanate, 1,3-bis(3-isocyanato-4-methylphenyl)-2,4-dioxodiazetidine, N,N'-bis(4-methyl-3-isocyanatophenyl)urea and tetramethylxylylene diisocyanate. Among these, preference is given to hexamethylene 1,6-diisocyanate.

The allophanates particularly preferred in the context of the present invention are compounds of the formula (VII)

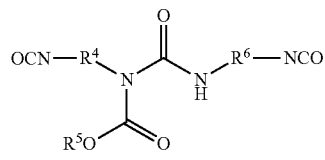

where $R^4$ and $R^6$ within the molecule may be the same or different and are each $C_1$-$C_6$-alkyl, preferably —$(CH_2)_6$—, and $R^5$ is $C_1$-$C_6$-alkyl.

Corresponding allophanates and the preparation thereof are described, for example, in EP 0 000 194A, the disclosure of which in this regard is incorporated by reference into the present invention. The aforementioned compounds are commodity chemicals and are available, for example from Bayer MaterialScience AG.

Carbodiimides in the context of the invention are preferably compounds of the formula (VIII)

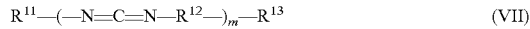  (VII)

in which m is an integer from 1 to 500, $R^{12}$ is $C_1$-$C_{18}$-alkylene, $C_5$-$C_{18}$-cycloalkylene, arylene and/or $C_7$-$C_{18}$-aralkylene, $R^{11}$ is $R^{12}$—NCO, $R^{12}$—NHCONHR$^9$, $R^{12}$—NHCONR$^9$R$^4$ or $R^2$—NHCOOR$^8$ and $R^{13}$ stands —NCO, —NHCONHR$^9$, —NHCONR$^9$R$^7$ or —NHCOOR$^8$ stands, where, in $R^{11}$, $R^9$ and $R^7$ are the same or different and are each independently a $C_1$-$C_6$-alkyl, $C_6$-$C_{10}$-cycloalkyl or $C_7$-$C_{18}$-aralkyl radical and $R^8$ has one of the definitions of $R^{11}$ or is a polyester or polyamide radical or —$(CH_2)_h$—O—$[(CH_2)_k$—O$]_g$—$R^{10}$, with h=1-3, k=1-3, g=0-12, where $R^{10}$ is defined as H or $C_1$-$C_4$-alkyl.

Likewise usable are also mixtures of carbodiimides of the formula (VIII), including the corresponding oligomers and/or polymers, preference being given to polymeric carbodiimides.

The compounds of the formula (VIII) are commercially available, for example from Rhein Chemie Rheinau GmbH, or can be prepared by the processes familiar to the person skilled in the art, as described, for example, in DE-A-11 30 594 or U.S. Pat. No. 2,840,589, or by the condensation of diisocyanates with elimination of carbon dioxide at elevated temperatures, for example at 40° C. to 200° C., in the presence of catalysts. Useful catalysts have been found to be preferably strong bases or phosphorus compounds. Preference is given to using phospholene oxides, phospholidines or phospholine oxides, and the corresponding sulfides. It is also possible to use, as catalysts, tertiary amines, basic metal compounds, metal carboxylates and non-basic organometallic compounds.

The aforementioned compounds are commodity chemicals and are available, for example from Rhein Chemie Rheinau GmbH.

Blocked activators, preferably blocked with lactams, more preferably caprolactam, or activators blocked with phenols, oximes and/or epoxides are preparable, for example, via the reaction of at least one compound of the formulae (I) to (VI) with at least one lactam, caprolactam, phenol, oxime and/or epoxide at temperatures of 80 to 100° C. by the processes familiar to those skilled in the art.

For production of the cast polyamides, in one embodiment of the invention, based on lactam, preference is given to using the following proportions:

0.1 to 3% by weight, preferably 0.2 to 1.5% by weight, of the inventive composition and 0.1 to 2% by weight, preferably 0.5 to 1% by weight, of activator.

In a preferred embodiment of the invention, the cast polyamide is obtainable by the polymerization of lactam, preferably caprolactam, with 0.1 to 3% by weight of the inventive composition comprising sodium lactamate a) as a preferably 18-20% by weight caprolactam solution containing 0.1 to 5% by weight, preferably 0.5-4% by weight, more preferably 1.5-2.5% by weight, of sodium aminocapronate and 0.1 to 2% by weight of at least one representative selected from the group of hexamethylene 1,6-diisocyanate with caprolactam-blocked hexamethylene 1,6-diisocyanate, biuret of the formula (V) with p=6 and/or a uretdione based on 2,4-diisocyanatotoluene as activator.

In a further preferred embodiment of the invention, the mixture for production of cast polyamides additionally comprises at least one further additive and assistant, selected from fillers and/or reinforcers, polymers and/or further additives.

Fillers and/or reinforcers in the context of the invention are organic or inorganic fillers and/or reinforcers. Preference is given to inorganic fillers, especially kaolin, chalk, wollastonite, talc, calcium carbonate, silicates, titanium dioxide, zinc oxide, graphite, graphenes, glass particles (e.g. glass beads), nanoscale fillers (such as carbon nanotubes), carbon black, sheet silicates, nanoscale sheet silicates, nanoscale aluminum oxide ($Al_2O_3$), nanoscale titanium dioxide ($TiO_2$) and/or nanoscale silicon dioxide ($SiO_2$).

Preference is further given to the use of fibrous materials as filler and/or reinforcer. The fillers and/or reinforcers are generally selected from the group comprising minerals in a grain size customary for thermoplastics applications, especially kaolin, chalk, wollastonite or talc, carbon fibers or glass fibers, preferably ground glass fibers, more preferably glass fibers and carbon fibers.

More preferably, one or more fibrous materials are used, selected from known inorganic reinforcing fibers, especially boron fibers, glass fibers, carbon fibers, silica fibers, ceramic fibers and basalt fibers; organic reinforcing fibers, especially aramid fibers, polyester fibers, nylon fibers, polyethylene fibers; and natural fibers, especially wood fibers, flax fibers, hemp fibers and sisal fibers. Especially preferred is the use of glass fibers, especially chopped glass fibers, carbon fibers, aramid fibers, boron fibers, metal fibers and/or potassium titanate fibers.

More particularly, it is also possible to use mixtures of said fillers and/or reinforcers. Particular preference is given to selecting, as fillers and/or reinforcers, glass fibers and/or glass particles, especially glass beads.

The amount of fillers and/or reinforcers to be used is preferably 30 to 90% by weight, especially 30-80% by weight, preferably 30 to 50% by weight, and further preferably from 50 to 90% by weight.

Polymers in the context of the invention are: polystyrene, styrene copolymers, especially styrene, acrylonitrile copolymers (SAN), acrylonitrile-butadiene-styrene copolymers (ABS) or styrene-butadiene copolymers (SB), polyphenylene oxide ethers, polyolefins, especially polyethylene (HTPE (high-temperature-polyethylene), LTPE (low-temperature-polyethylene), polypropylene or polybutene-1, polytetrafluoroethylene, polyesters, especially polyethylene terephthalate (PET); polyamides, polyethers, especially polyethylene glycol (PEG), polypropylene glycol or polyether sulfones (PESU or PES); polymers of monomers containing vinyl groups, especially polyvinyl chloride, polyvinylidene chlorides, polystyrene, impact-modified polystyrene, polyvinylcarbazole, polyvinyl acetate or polyvinyl alcohol, polyisobutylene, polybutadiene and/or polysulfones. It is additionally possible to use, as the polymer, copolymers consisting of the monomer units of the above-mentioned polymers.

In a further embodiment of the invention, the polymer to be used may contain groups suitable for formation of block and/or graft copolymers with the polymers formed from the monomers. Examples of such groups are epoxy, amine, carboxylic anhydride, oxazoline, carbodiimide, urethane, isocyanate and lactam groups. Polymers having carbodiimide groups are used when no carbodiimide is used as activator.

Any polymer present is present preferably in an amount of 0 to 40% by weight, preferably of 0 to 20% by weight, more preferably in an amount of 0 to 10% by weight.

In a preferred embodiment, inventive composition comprises further additives. Preference is given to using the additives in an amount of 0 to 5% by weight, more preferably of 0 to 4% by weight, most preferably of 0 to 3.5% by weight. Additives added may preferably be stabilizers, especially copper salts, dyes, antistats, filler oils, stabilizers, surface improvers, siccatives, demolding aids, separating agents, antioxidants, light stabilizers, PVC stabilizers, lubricants, polyols, flame retardants, blowing agents, impact modifiers and/or nucleating aids.

Suitable impact modifiers are especially polydiene polymers, preferably polybutadiene, polyisoprene, containing anhydride and/or epoxy groups. The polydiene polymer has a glass transition temperature below 0° C., preferably below −10° C., more preferably below −20° C. The polydiene polymer may be based on the basis of a polydiene copolymer with polyacrylates, polyethylene acrylates and/or polysiloxanes, and be prepared by means of the standard processes, preferably by emulsion polymerization, suspension polymerization, solution polymerization, gas phase polymerization.

In a further preferred embodiment of the invention, polyol is used as an additive to improve impact resistance. These are available, for example, from Rhein Chemie Rheinau GmbH under the Addonyl® 8073 name. Likewise usable are polyol triamines suitable for improving low temperature impact resistance. A suitable product is Addonyl® 8112. Preference is given to using the polyols in the concentration range of 1-20% by weight.

The optional addition of fillers and/or reinforcers and further additives may precede or coincide with the addition of catalyst and/or activator.

In a further execution of the present invention, the polymerization for production of cast polyamides can be performed by a suitable shaping process, preferably injection casting, stationary casting processes, rotary casting processes.

Injection casting, stationary casting processes, rotary casting processes are processes familiar to those skilled in the art.

The scope of the invention includes all general radical definitions, indices, parameters and illustrations mentioned above and below, and those mentioned in preferred ranges with one another, i.e. also any combinations between the respective ranges and preferred ranges.

The present invention further provides for the use of the inventive composition as a catalyst for production of cast polyamide.

In addition, the invention further provides for the use of the inventive composition for production of rollers, preferably for passenger elevators and semifinished products, preferably vessels, gears, tubes, bars and sheets for mechanical engineering and the automobile industry.

The examples which follow serve to illustrate the invention but have no limiting effect.

WORKING EXAMPLES

Reagents:
 Dry caprolactam (EP>69° C.) from Lanxess Deutschland GmbH
 Activator, a hexamethylene 1,6-diisocyanate (HDI) biuret, 70% in N-ethylpyrrolidone, commercially available from Rhein Chemie Rheinau GmbH
 Inventive composition as catalyst (A) with about 18% sodium caprolactamate and 2.0% sodium aminocapronate in caprolactam
 Composition according to the prior art as catalyst (B) with about 18% sodium caprolactamate in caprolactam, comparison Equipment:
 The apparatus used to prepare the melt consisted of:
 2 three-neck flasks (500 ml), heated in an oil bath
 2 precision glass stirrers with sleeves
 2 gas caps, 1 with and 1 without a tap
 1 vacuum pump with cold trap and manometer.
 The apparatus used to measure the temperature consisted of:
 Testo 175-T3 temperature measuring instrument with IR serial interface
 thermocouple to remain in the hardened sample
 600 ml beaker (high mold) and a
 heater for the beaker (metal block, oil bath).

Procedure and Measurement of Pot Life:
 Flask A was charged with 196.8 g of caprolactam and 3.2 g of activator, flasks B1/2 with 192 g of caprolactam and 8 g of catalyst (A) or (B).
 The melts from flask A and flasks B1/2 were prepared at 110-130° C. (±2° C.) in an oil bath under reduced pressure (<15 mbar) for 20 minutes.
 After venting with nitrogen, components from flask A and flasks B were combined in a three-neck flask, stirred briefly and transferred to the 600 ml beaker.
 The mold temperature (beaker) was 160° C. The polymerization time was generally 10-20 minutes.
 The opacity test was effected in a drying cabinet at 85° C. after a period of 3 h. The assessment was made visually.
 The assessment of the quality of the cast polyamides in relation to crystallinity and homogeneity was made on the basis of SEM images (scanning electron microscope).

| Catalyst in flask B1/2 | Pot life (s) | Opacity less (85° C., 3 h) | Crystallinity/homogeneity Cast polyamide |
|---|---|---|---|
| Catalyst A (inv.) | 380 | clear | high |
| Catalyst B (C) | 270 | very opaque | low |

Comparative example = comp.,
inventive = inv.

The mixtures according to the prior art generally have pot lives of <300 s, which leads to inhomogeneity and a low crystallinity in the cast polyamide. In addition, the melts containing the catalyst already polymerize in the preparation vessel and thus block the filters upstream of the casting mold.

The examples show that the inventive catalyst has pot lives of well above 300 s. The inventive compositions additionally do not become opaque.

In this way, it is also possible to produce high-volume, high-quality cast polyamide parts. Furthermore, it is possible to distinctly improve the quality of the cast polyamides thus produced in terms of crystallinity and homogeneity.

What is claimed is:

1. A composition comprising:
   a) at least one lactamate;
   b) at least one alkali metal salt of aminocapronates and/or aminolaurates; and
   c) at least one lactam,
   wherein constituents a) and b) are present in a ratio of 3:1 to 50:1, and the proportion of lactam c), based on constituents a) and b), is less than or equal to 99% by weight.

2. The composition as claimed in claim 1, wherein the lactamate is at least one compound selected from the group of the alkali metal aluminodilactamates, alkali metal lactamates, and alkaline earth metal lactamates.

3. The composition as claimed in claim 1, wherein the alkali metal salt is sodium aminocapronate and/or sodium aminolaurate.

4. The composition as claimed in claim 1, wherein the at least one lactam corresponds to the general formula

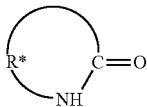

where R* is an alkylene group having 3 to 13 carbon atoms.

5. A process for preparing the composition as claimed in claim 1, the process comprising:
   preparing the at least one lactamate by reaction of at least one lactam with alkali metal and/or alkaline earth metal alkoxides in the presence of the at least one alkali metal salt to produce a mixture containing alcohol; and
   subsequently or simultaneously removing the alcohol from the mixture.

6. The process as claimed in claim 5, further comprising preparing the alkali metal salt in situ by addition of acids, water and/or alkali metal hydroxides to a).

7. A cast polyamide produced by a process comprising polymerization of lactams with at least one composition of claim 1 at temperatures of 80-180° C., optionally in the presence of activators and/or further additives and assistants.

8. A process for producing cast polyamides, the process comprising polymerizing lactams with at least one composition of claim 1 at temperatures of 80-120° C. in the presence of activators and optionally further additives and assistants.

9. A process for producing cast polyamides, the process comprising including the composition as claimed in claim 1 as a catalyst for the production of cast polyamide.

10. A method for producing articles of manufacture, the method comprising producing from the composition as claimed in claim 1, at least one of rollers, vessels, gears, tubes, bars and sheets for mechanical engineering, passenger elevators and the automobile industry.

11. The composition as claimed in claim 1, wherein:
    the lactamate is at least one compound selected from the group of the alkali metal aluminodilactamates, alkali metal lactamates and alkaline earth metal lactamates.

12. The composition as claimed in claim 11, wherein:
    the heteroatoms are amino groups, and the salt of an organic acid substituted by heteroatoms comprises aminocapronates and/or aminolaurates;
    the composition further comprises c) at least one lactam of the general formula

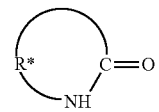

where R* is an alkylene group having 3 to 13 carbon atoms;
constituents a) and b) are present in a ratio of 9:1; and
the proportion of lectern c), based on constituents a) and b), is 50-85% by weight.

13. The process as claimed in claim 5, further comprising, after removal of the alcohol, adding at least one further lactam.

14. The process as claimed in claim 5, wherein, the lactamate a) is prepared by reaction of caprolactam with sodium methoxide in the presence of sodium aminocapronate and/or sodium aminolaurate.

15. The process as claimed in claim 14, further comprising, after removal of the alcohol, adding additional caprolactam.

* * * * *